(12) United States Patent
Abita et al.

(10) Patent No.: US 6,228,064 B1
(45) Date of Patent: *May 8, 2001

(54) INTRAVENOUS ANCHOR SYSTEM (IVFAS)

(75) Inventors: Joseph L. Abita, Boyds; Daniel A. Ossing, Catonsville, both of MD (US)

(73) Assignee: The Johns Hopkins University, Baltimore, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/823,283

(22) Filed: Mar. 21, 1997

(51) Int. Cl.$^7$ ...................................................... A61M 5/32
(52) U.S. Cl. ............................................................ 604/179
(58) Field of Search ................................... 604/174, 175, 604/177, 178, 179, 180; 128/DIG. 26; 122/DIG. 6

(56) References Cited

U.S. PATENT DOCUMENTS

| | | | | |
|---|---|---|---|---|
| 2,606,555 | * | 8/1952 | Solomon | 604/180 X |
| 3,167,072 | * | 1/1965 | Stone et al. | 604/179 |
| 4,397,647 | * | 8/1983 | Gordon | 604/180 |
| 4,416,664 | * | 11/1983 | Womack | 604/174 |
| 4,453,933 | | 6/1984 | Speaker | 604/179 |
| 4,585,443 | * | 4/1986 | Kaufman | 604/174 |
| 5,000,741 | * | 3/1991 | Kalf | 604/180 |
| 5,167,630 | * | 12/1992 | Paul | 604/174 X |
| 5,188,608 | | 2/1993 | Fritts | 604/179 |
| 5,354,282 | | 10/1994 | Bierman | 604/180 |
| 5,413,562 | * | 5/1995 | Swauger | 604/174 X |
| 5,578,013 | | 11/1996 | Bierman | 604/180 |
| 5,709,665 | * | 1/1998 | Vergano et al. | 604/174 |

* cited by examiner

Primary Examiner—Manuel Mendez
(74) Attorney, Agent, or Firm—Carla Magda Krivak

(57) ABSTRACT

An intravenous feed anchor system (IVFAS) that allows for unconstrained movement of a patient and IV configuration. The IVFAS includes an IV line clamp device for clamping a section of an IV line, an attach device for receiving and securing the IV line clamp device, and a securing device for securing an adjustable tie down to a patient. The IV attach device receives the IV line clamp device in a free floating condition. This prevents excessive motion and forces, caused by reasonable, unexpected or unusual conditions, from removing, or interrupting IV treatment. The IVFAS also keeps the section of the IV line between the anchor and insertion points in close proximity to the patient. This eliminates large IV line loops which have a tendency to snag or get pulled from environmental animate and inanimate objects. The IVFAS is quickly and easily attached and detached.

22 Claims, 4 Drawing Sheets

INTRAVENOUS ANCHOR SYSTEM (IVFAS)

BACKGROUND OF THE INVENTION

1. Field of the Invention

The present invention relates to a feed anchor system, and more particularly, to an intravenous feed anchor system (IVFAS) for preventing certain environmental forces from interrupting intravenous (IV) treatment due to unintentional removal or breaking of a patient's IV inserted needle.

2. Description of the Related Art

In general, nutrients or medications are administered using intravenous (IV) lines and systems. Frequently, IV treatment is interrupted by unintentional movement, blockage or removal of the IV supply line from the patient due to "pulling forces" exerted on the IV supply line. This occurs particularly with active children and patients in considerable distress. The "pulling forces" can be a result of the IV line being snagged or pulled by environmental animate or inanimate objects.

Health care providers normally secure the position of an IV line using adhesive tape to fix it against a patient's skin. The inserted needle is also reinforced against movement using tape. However, taping has limited effectiveness and undesirable features, such as irritating skin, causing pain when removed, etc. As noted above, patients can move in a manner that inadvertently pulls on the tubing or catches the tubing on an object. In addition, some patients, such as small children or those with mental illness, will knowingly or unknowingly tug on an IV line. In non-critical situations, this is an inconvenience and results in patient discomfort. In critical situations, interruption of the IV supply can result in health risks, discomfort, pain, or even death. Further, the IV must be reinserted when the IV is pulled from a patient's body. This increases the number of skin punctures and increases the risk of infection and contingencies. It is also costly with respect to additional staff demands and treatment.

Numerous IV support and anchoring devices have been proposed to overcome the above-mentioned problem. An example of such a device includes U.S. Pat. No. 4,453,933 which discloses an arrangement of an IV feeding tube affixed to a strap wrapped loosely around a patient's limb at a location intermediate to the ends of the tube so that a loop is formed. Thus, any tension applied between a fluid reservoir and an intermediate point on the IV tube is transmitted to the strap and then to a patient's limb (an arm) and not to the IV line. A protective sleeve covers the limb and the IV device to prevent patient access to the IV device. U.S. Pat. Nos. 5,354,282 and 5,578,013 disclose an anchoring system that includes a flexible, adhesive base pad that supports an IV tube clip and a retainer. The retainer slides relative to the base pad to precisely position the retainer relative to the IV line. U.S. Pat. No. 5,188,608 discloses a protective stabilizing sleeve for an IV needle. The sleeve is secured around a patient's arm or hand. The sleeve protects the site where the needle is inserted and stabilizes the connecting tube.

However, the prior art devices fall short of desired ease of application and performance and are not always effective in preventing inadvertent IV line removal. Further, the prior art devices are relatively expensive, difficult to manufacture and difficult to use.

SUMMARY OF THE INVENTION

It is an object of the present invention to provide an easy to use intravenous anchor assembly that includes an IV line attach device, a patient attach device and a device to secure an adjustable tie down.

It is another object of the present invention to provide an IV feed anchor tube clamp (IVFATC) at any exposed section of an IV line.

It is a further object of the present invention to provide a device for preventing certain environmental forces from interrupting IV treatment due to unintentional removal or breakage of a patient's IV inserted needle.

It is yet another object of the present invention to provide an intravenous feed anchor system for application on many parts of a body.

It is still another object of the present invention to provide a low cost, highly effective, throwaway intravenous feed anchor system.

The above objects of the present invention are obtained by providing an intravenous anchor assembly including an IV line clamp device clamping an IV line, an attach device for receiving and securing the IV line clamp device and a securing device for securing an adjustable tie down to a patient. The securing device includes a high surface friction strap. The attach device includes a friction interface, a first rotatable member for receiving a first end of the strap, a second rotatable member, opposite the first rotatable member, for receiving and securing it second end of the strap, and a latching arm which secures the IV line clamp device. The friction interface is a high friction material which prevents the IVFAS from sliding on a patient's skin.

The latching arm includes a cantilever beam for receiving the IV attach device. The cantilever beam can be latched and unlatched to perform adjustments.

The present invention also provides a method for securing an intravenous anchor assembly to a patient. The method includes securing a first end of a strap into a first opening in an attach device, wrapping the strap around an area of a patient's body, securing a second end of a strap into a second opening, opposite the first opening, in the attach device, inserting an IV line section into a receiving region in an IV line clamp device, locking the IV line section in the receiving section of the IV line clamp device, inserting the IV line clamp device onto a top beam member of the attach device and latching the top beam member to secure the IV line clamp device to the attach device. The IV line clamp device is latched in a free floating condition. The IV line section can be repositioned by unlocking the IV clamping device from the secured IV attach device.

These objects, together with other objects and advantages which will be subsequently apparent, reside in the details of construction and operation as more fully described and claimed hereinafter, reference being had to the accompanying drawings forming a part hereof, wherein like reference numerals refer to like parts throughout.

DESCRIPTION OF THE PREFERRED EMBODIMENTS

The design of the intravenous feed anchor system (hereinafter referred to as IVFAS) of the present invention ameliorates or eliminates potential problems associated with the administration of intravenous (IV) nutrients or medications. These problems include interrupted or blocked treatment, removal of an IV supply line from a patient due to "pulling forces" exerted on an IV supply line, or needle breakage.

Figure 1:
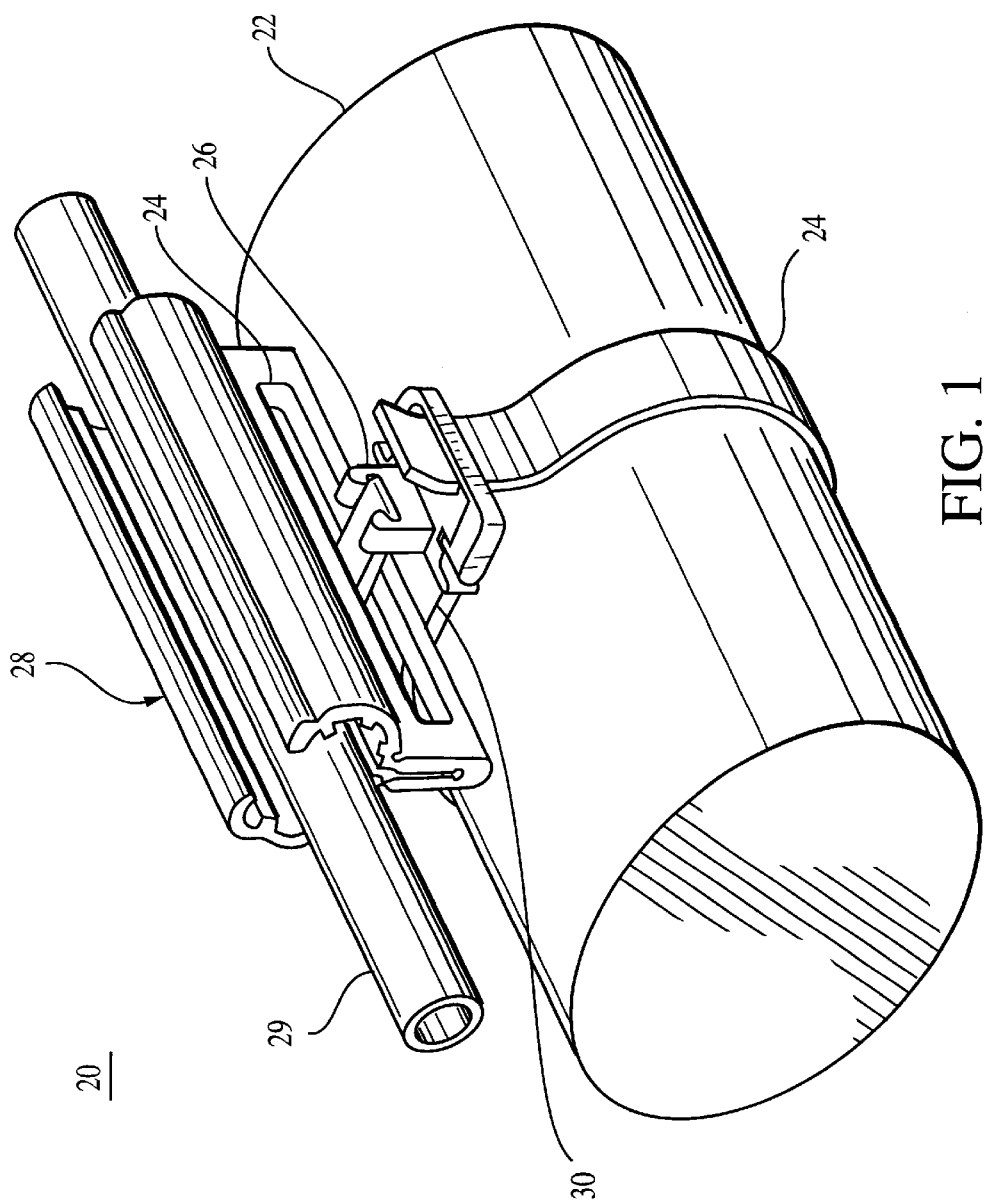
FIG. 1 is a diagram of an intravenous feed anchor system (IVFAS), according to the present invention, attached to a limb of a patient.

FIG. 1 is a diagram of an example of an IVFAS 20 according to the present invention. As shown, the IVFAS 20 is secured around any portion of a patient's body 22 by an attach strap 24. The attach strap 24 can be cut from a roll of material so that it is customized to the patient's limb, such as, but not limited to, an arm, wrist, hand, leg, abdomen, etc. The attach strap 24 can be made from a material, including an elastic material of some type, that has a high friction surface contacting a patient's skin. The attach strap 24 secures an IVFABL 26 to the patient. The IVFABL 26 secures an IVFATC 28. The IVFATC 28 secures an IV supply line 29. A friction interface 30 is located beneath the IVFABL 26 to resist sliding motion of the IVFAS 20 from its place on the patient's body 22.

Figure 2:
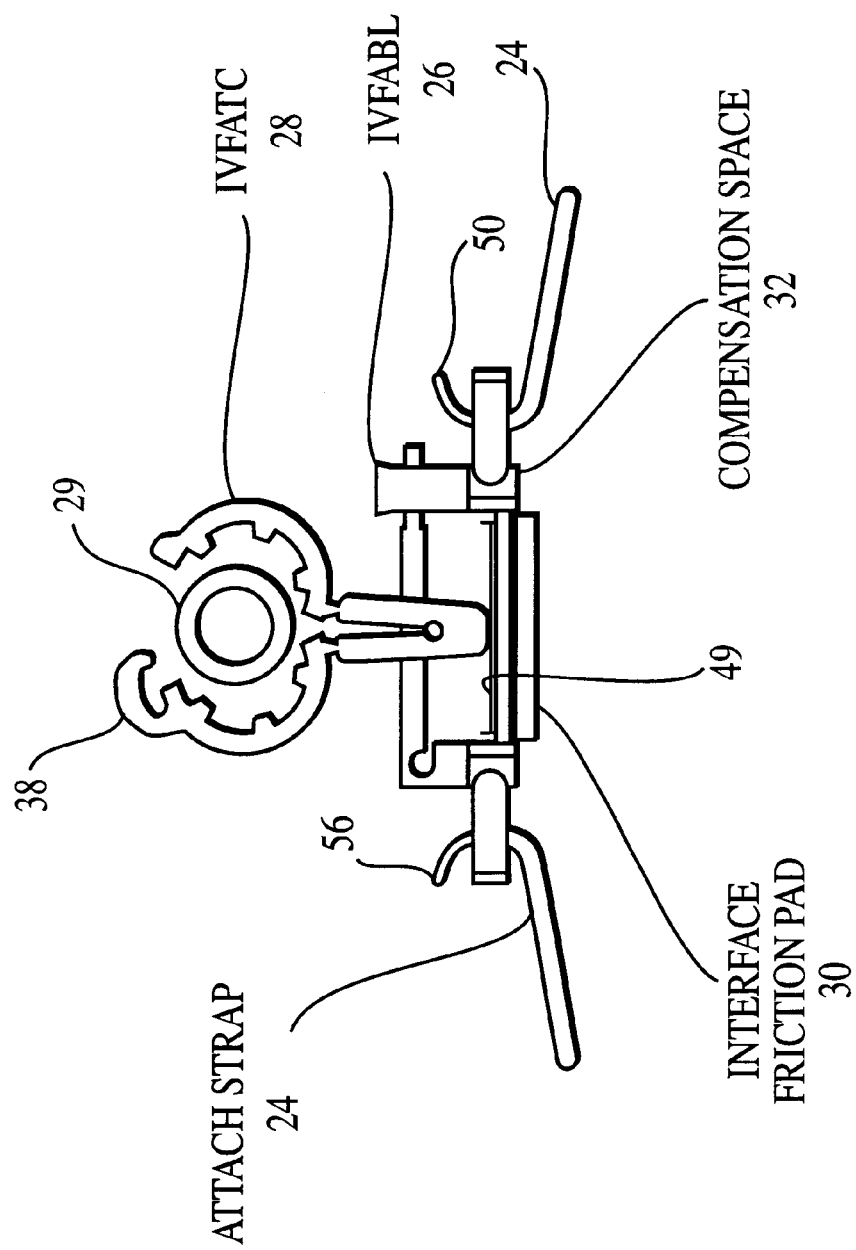
FIG. 2 is a side view of the intravenous feed anchor system in FIG. 1 according to the present invention.

FIG. 2 is a side view of the IVFAS 20 shown in FIG. 1. The side view shows a strap compensation space 32 between the friction interface 30 and the attach strap 24. The IVFAS 20 will now be explained in detail with respect to the remaining drawings.

Figure 3:
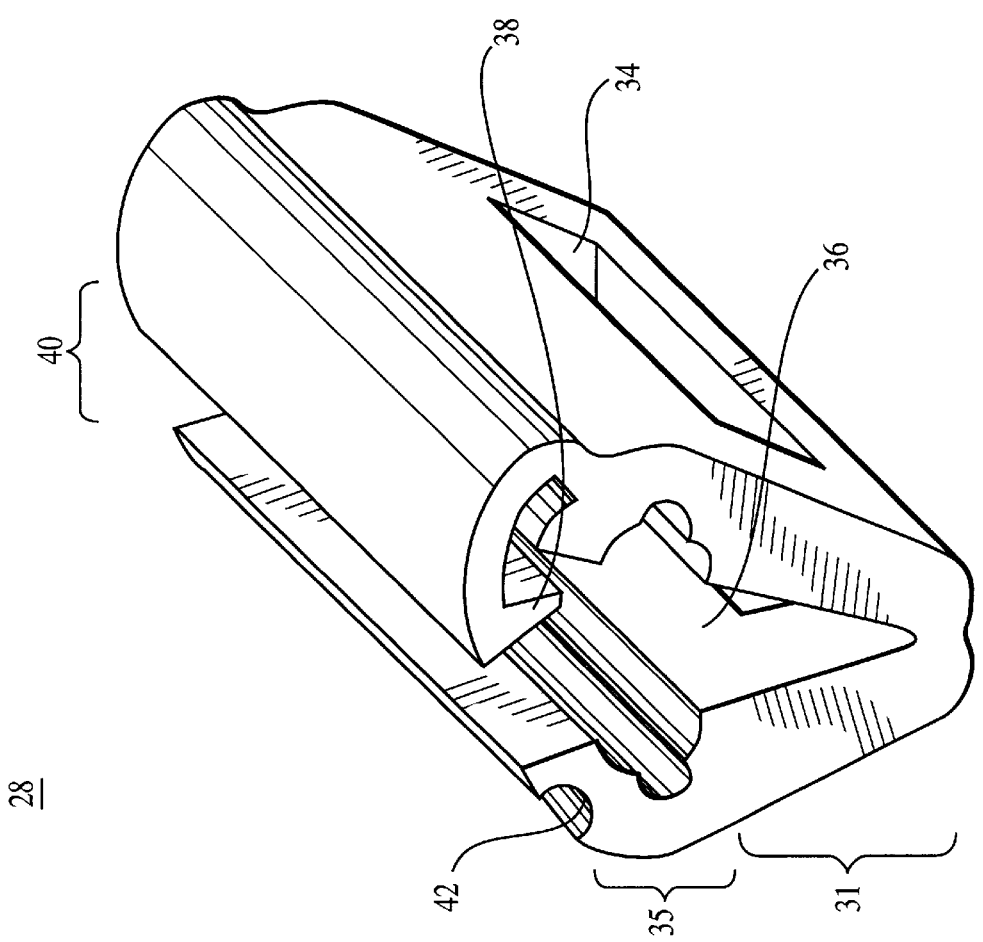
FIG. 3 is a diagram of an example of an intravenous feed anchor tube clamp (IVFATC) that can be used in the intravenous feed anchor system of the present invention.

FIG. 3 is a diagram of an example of an IVFATC 28 that can be used in the IVFAS 20 of the present invention. A lower portion 31 of the IVFATC 28 of the IVFAS 20 includes a slot 34 that runs in a lengthwise direction. An upper portion 35 includes an opening 36 for receiving the IV supply line 29. The IV supply line 29 is placed in the opening 36 in the IVFATC 28 and the IVFATC 28 is then snapped closed. A latch member 38 on a top portion 40 of the upper portion 35 of the IVFATC 28 is inserted into a side groove 42 on the upper portion 35 of the IVFATC 28 to secure the IV supply line 29. Because the IVFATC 28 can be removed and re-attached to readjust it or to correct any misplacement it can be placed along any exposed section of the IV supply line 29. The internal circumference of the opening 36 in the IVFATC 28 for receiving the IV supply line 29 is undersized and shaped in relation to the IV supply line 29. The IVFATC 28 can accommodate a number of IV supply line 29 diameters. Further, choosing the length-to-diameter ratio of the IVFATC 28 to maintain axial positioning of the IV supply line 29 discourages off-axis force deformation which results in kinking of the IV supply line 29.

A material selected for the IVFATC 28 provides a "natural adhesion" to the IV supply line 29 material. This prevents the IV supply line 29 from sliding under reasonable forces while in the grip of the IVFATC 28 without the use of adhesives, and without restricting fluid flow through the IV supply line 29. An example of such a material that meets this criteria is Ciba Geigy RP6442. The invention, however, is not limited to this material.

Figure 4:
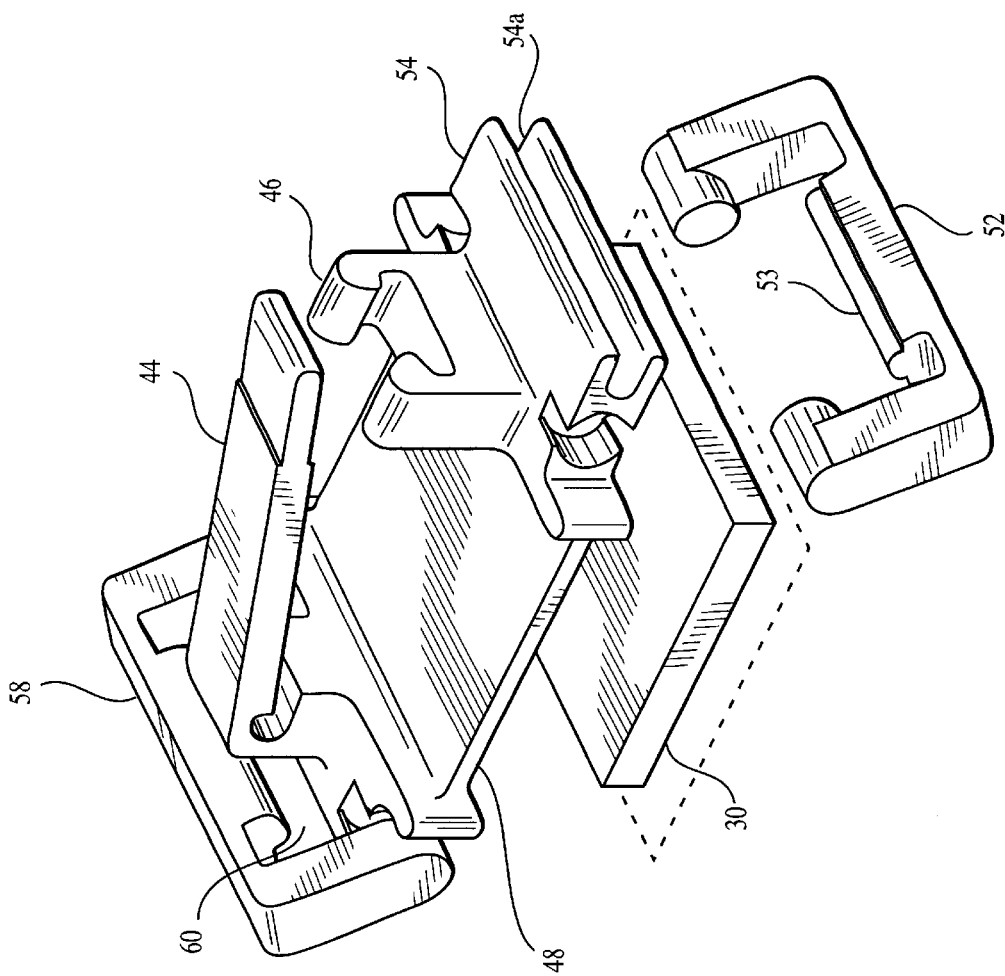
FIG. 4 is a diagram of an example of an intravenous feed anchor body link (IVFABL) that can be used in the intravenous feed anchor system of the present invention.

FIG. 4 is a diagram of an example of an IVFABL 26 that can be used in the present invention. The IVFABL 26 secures the IVFATC 28 by way of a latching cantilever beam 44. That is, the slot 34 in the IVFATC 28 slides over the latching cantilever beam 44 of the IVFABL 26. The latching cantilever beam 44 is then pressed down and snapped shut so that it engages and locks in a retaining clasp 46 on one side of is the IVFABL 26. This design allows the IVFATC 28 to be in a free-floating condition and the latching cantilever beam 44 to accommodate flexure of the base plate 48 of the IVFABL 26 in accordance with deformations encountered in conforming to body contours and to tugs and pulls applied to the IV supply line 29. A suitable material for the IVFABL 26 can be a plastic such as, but not limited to, Dexter Hysol EA 9309-3NA.

The friction interface 30 can be located in a space 32 on a center section 49 of the IVFABL 26 base 48. The center section 49 of the IVFABL 26 base 48 is thinner than at its edges. The friction interface 30 of the IVFABL 26 contacts the patient's skin and maintains the position of the IVFAS 20 to the patient. Flexure of the IVFABL 26 allows for conformance to body surfaces attached to the IVFAS 20. The friction interface 30 includes, for example, a material that has a high coefficient of friction, such as compliant rubber, or a non-allergenic adhesive coating that is easily removed using standard home, clinic or hospital solutions, such as alcohol. The friction interface 30 has an extended thickness provided within the compensation space 32 to allow for the attach strap 24 thickness. This eliminates step transitions affecting performance and patient comfort. The friction interface 30 can include a single material having an acceptable frictional property, a part integral to the IVFABL 26 and made of a molded laminate or composite such that the portion contacting the patients' skin has a high coefficient of friction, or as in the above example, is a separate piece of material.

The IVFABL 26 attach strap 24 has a first end 50 (see FIG. 2) inserted into a first rotatable cinching member 52 including a raised semicircular portion 53. That is, the first end 50 of the attach strap 24 is inserted into a space between the first rotatable cinching member 52 and a first beam latch member 44 of the IVFABL 26. The first beam latch member 54 includes a slot 54a for receiving the raised semicircular portion 53. The first rotatable cinching member 52 is rotated into the base plate 48 of the IVFABL 26 engaging the slot 54a of the first rotatable cinching member 52 capturing the attach strap 24 and locking securely by the mating of the raised semicircular portion 53 with the slot 54a, thereby securing the first end 50 of the attach strap 24. The attach strap 24 is then wrapped around a desired portion of the patient's body 22. For example, the attach strap 24 can be wrapped around an arm, leg, wrist, abdomen, etc. The free or second end 56 of the attach strap 24 is then passed through a second rotatable cinching member 58, opposite the first rotatable cinching member 52 and a second beam latch member 60 which includes a slot (not shown) for receiving a raised semicircular portion of the second rotatable cinching member 52. The second end 56 of the attach strap 24 is then pulled to a desired tension and secured by rotating the second rotatable cinching member 58 into the base plate 48 of the IVFABL 26 as explained above. As noted above, the attach strap 24 can be separately available on a roll. A length of the attach strap 24 can be cut to a desired length according to the patient's size and application requirements. The IVFABL 26 can be removed from the patient by releasing one or more of the rotatable cinching members. The rotatable cinching members can include, but are not limited to, a cylinder-in-groove compression mechanism.

Threading each end of the attach strap 24 into a fully enclosed space formed between each of the rotatable cinching members and the latching cantilever beam 44 aids strap attachment by constraining the attach strap 24 and acting as a fulcrum for the setting of strap tension. Further, adjustments are performed or errors are corrected by latching and unlatching the first or second rotatable cinching members 52 and 58 numerous times.

The design of the IVFAS 20 allows easy attachment and detachment by a single person. In addition, it also provides an intravenous anchor system that remains secure, when attached to a patient, without interruption of fluid flow or accidental removal from a patient. The parts of the IVFAS 20 are suited to volume production, packaging, and distribution at low cost. For example, the device can be made of injection molded plastic material that makes it an inexpensive, one-use, throw-away item. Further, the dimensions of the IVFABL 26 are chosen to work properly on either smaller girths such as a child's wrist or ankle, or larger girths such as those associated with adults. That is, the length dimension is different according to use.

Thus, the present invention provides an anchor system that is comfortable, is easy to use, can be used at many body positions, is sterile, reliable, disposable, affordable and mass producible.

The foregoing is considered as illustrative only of the principles of the invention. The device is not necessarily limited to an IV anchor system, but may be used to anchor other objects as seen fit. Further, since numerous modifications and changes will readily occur to those skilled in the art, it is not desired to limit the invention to the exact construction and applications shown and described. That is, various configurations can be used for the IVFABL 26 and IVFATC 28. In addition, various materials can be employed, depending on use, availability, preference, cost, etc. Accordingly, all suitable modifications and equivalents may be resorted to, falling within the scope of the invention and the appended claims and their equivalents.

What is claimed is:

1. An intravenous (IV) anchor assembly, comprising:
   IV line clamp means for clamping an IV line;
   attach means for receiving and holding said IV line clamp means in a free-floating condition, said attach means comprising:
   a base plate;
   a friction interface coupled to said base plate, said friction interface includes a high friction material located on at least one side for contacting a patient;
   a first rotatable cinching member, coupled to said base plate, for receiving a first end of said securing means;
   a first beam latch member, connected to said first rotatable cinching member, for latching said first end of said securing means;
   a second rotatable cinching member, coupled to said base plate and located opposite said first rotatable member, for receiving a second end of said securing means;
   a second beam latch member, connected to said second rotatable cinching member, for latching said second end of said securing means; and
   latching means, attached to said attach means, for latching said IV line clamp means; and
   securing means, coupled to said attach means, for securing said attach means to the patient, said securing means comprising a strap.

2. An IV anchor assembly according to claim 1, wherein said high friction material comprises a non-allergenic adhesive property.

3. An IV anchor assembly according to claim 1, wherein said latching means comprises a latching cantilever beam and wherein said IV line clamp means includes a slot therein for receiving said latching cantilever beam.

4. An IV anchor assembly according to claim 3, wherein said latching cantilever beam locks said IV line clamp means in a free-floating condition.

5. An IV anchor assembly according to claim 4, wherein said latching cantilever beam can be unlatched and re-latched.

6. An IV anchor assembly according to claim 1, wherein said IV line clamp means comprises:
   a member for receiving the IV line; and
   latch means for securing the received IV line.

7. An IV anchor assembly according to claim 6, wherein said latch means is integrally formed with said member.

8. An IV anchor assembly according to claim 7, wherein said latch means comprises a material selected from one of a composite and laminate material.

9. A method for securing an assembly, said method comprising the steps of:
   a) securing a first end of a strap into a first opening in an attach means;
   b) securing a second end of a strap into a second opening, opposite the first opening, in the attach means;
   c) inserting an object in a receiving region in a clamp means;
   d) locking the object in the receiving region of the clamp means;
   e) inserting the clamp means onto a top beam member of the attach means;
   f) latching the top beam member to secure the clamp means to the attach means.

10. A method according to claim 9, wherein said step f) comprises latching the secured clamp means in a free floating condition.

11. A method according to claim 10, further comprising a step g) of unlocking the object from the clamp means and repositioning the object.

12. A method for securing an intravenous (IV) anchor assembly to a patient, said method comprising the steps of:
   a) securing a first end of a strap into a first opening in an attach means;
   b) wrapping the strap around an area of a patient's body;
   c) securing a second end of a strap into a second opening, opposite the first opening, in the attach means;
   d) inserting an IV line section into a receiving region in an IV line clamp means;
   e) locking the IV line section in the receiving region of the IV line clamp means;
   f) inserting the IV line clamp means onto a top beam member of the attach means; and
   g) latching the top beam member to secure the IV line clamp means to the attach means.

13. A method according to claim 12, wherein said step g) includes latching the secured IV line clamp means in a free floating condition.

14. A method according to claim 13, further comprising a step h) of unlocking the IV line section from the secured IV line clamp means for repositioning the IV line section.

15. An anchor assembly comprising:
   clamp means for clamping an object;
   securing means, for securing the anchor assembly, said securing means comprising a flexible strap; and
   attach means for receiving and holding said clamp means in a free-floating condition, said attach means comprising:
   a base plate;

a friction interface coupled to said base plate;

a first rotatable member, coupled to said base plate, for receiving a first end of said securing means;

a first beam latch member, connected to said first rotatable member, for latching said first end of said securing means;

a second rotatable member, coupled to said base plate and located opposite said first rotatable member, for receiving a second end of said securing means;

a second beam latch member, connected to said second rotatable member, for latching said second end of said securing means; and latching means, attached to said attach means, for latching said clamp means.

16. An anchor assembly according to claim 15, wherein said latching means comprises a rotating cantilever beam; and said clamp means comprises:

a member for receiving the object;

securing means for securing the received object; and a slot for receiving said rotating cantilever beam.

17. An intravenous (IV) anchor assembly according to claim 1, wherein said IV anchor assembly is scaleable in form and function to accommodate any IV type.

18. An IV anchor assembly according to claim 1, wherein said first beam latch member has a slot therein for receiving said first rotatable cinching member and wherein said second beam latch member has a slot therein for receiving said second rotatable cinching member.

19. A method according to claim 9, further comprising accommodating any type of IV.

20. An anchor assembly according to claim 15, wherein said anchor assembly is scaleable in form and function to accommodate any IV type.

21. An anchor assembly according to claim 15, wherein said first beam latch member has a slot therein for receiving said first rotatable member and wherein said second beam latch member has a slot therein for receiving said second rotatable member.

22. An intravenous (IV) anchor assembly, comprising:

IV line clamp means for clamping an IV line;

attach means for receiving and holding said IV line clamp means in a free-floating condition; and securing means, coupled to said attach means, for securing said attach means to a patient, said securing means comprising a strap, said attach means comprises:

a base plate;

a friction interface coupled to said base plate;

a first rotatable cinching member, coupled to said base plate, for receiving a first end of said securing means;

a first beam latch member, connected to said first rotatable cinching member, for latching said first end of said securing means;

a second rotatable cinching member, coupled to said base plate and located opposite said first rotatable member, for receiving a second end of said securing means;

a second beam latch member, connected to said second rotatable cinching member, for latching said second end of said securing means; and latching means, attached to said attach means, for latching said IV line clamp means.

* * * * *